(12) United States Patent
Wada et al.

(10) Patent No.: US 8,919,546 B2
(45) Date of Patent: Dec. 30, 2014

(54) MOISTURE-PROOF CONTAINER

(75) Inventors: Kiyoshi Wada, Tokyo (JP); Masahiro Yoshida, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 54 days.

(21) Appl. No.: 13/510,496

(22) PCT Filed: Mar. 8, 2012

(86) PCT No.: PCT/JP2012/001586
§ 371 (c)(1),
(2), (4) Date: May 17, 2012

(87) PCT Pub. No.: WO2012/120887
PCT Pub. Date: Sep. 13, 2012

(65) Prior Publication Data
US 2013/0334074 A1 Dec. 19, 2013

(30) Foreign Application Priority Data

Mar. 8, 2011 (JP) .................................. 2011-050596
Mar. 6, 2012 (JP) .................................. 2012-049383

(51) Int. Cl.
*F17C 11/00* (2006.01)
*B65D 81/26* (2006.01)
(52) U.S. Cl.
CPC .............. *B65D 81/26* (2013.01); *B65D 81/266* (2013.01)
USPC .............................. 206/204; 206/449; 53/400
(58) Field of Classification Search
CPC .. B65D 81/264; B65D 81/265; B65D 81/266; B65D 81/268; B65D 81/26
USPC ............. 206/204, 540, 528, 538, 449; 53/400
See application file for complete search history.

(56) References Cited

U.S. PATENT DOCUMENTS 3,826,358 A * 7/1974 Butler et al. ................... 206/204
5,114,003 A * 5/1992 Jackisch et al. ............... 206/204

(Continued)

FOREIGN PATENT DOCUMENTS

EP 2077237 7/2009
FR 2 694 270 2/1994

(Continued)

OTHER PUBLICATIONS

Extended European Search Report dated Feb. 27, 2013 issued in corresponding European Patent Application No. 12719891.9-1708/2573007 (6 pages).

(Continued)

*Primary Examiner* — Mickey Yu
*Assistant Examiner* — Chun Cheung

(57) ABSTRACT

A moisture-proof container including: a container body; a lid hermetically closing the container body to be openable and closable; and a desiccant storage case that is put on a bottom portion of the container body. The desiccant storage case includes: an inner case having an opening at one end; a desiccant stored in the inner case; and a moisture transmission dustproof sheet to seal the opening of the inner case. The inner case has, at an outer circumferential wall thereof, a groove connecting between an open end and a bottom portion, the container body includes a base on a bottom plate, and the desiccant storage case is put in the container body such that the moisture transmission dustproof sheet abuts the base, and a gap is formed between the bottom plate of the container body, and the moisture transmission dustproof sheet.

6 Claims, 14 Drawing Sheets

(56) References Cited

U.S. PATENT DOCUMENTS

| | | | |
|---|---|---|---|
| 5,788,064 A * | 8/1998 | Sacherer et al. | 206/204 |
| 6,571,942 B2 * | 6/2003 | Riemenschneider et al. | 206/204 |
| D491,275 S | 6/2004 | Walters et al. | |
| D555,490 S | 11/2007 | Liu | |
| D559,677 S | 1/2008 | Laib | |
| D598,738 S | 8/2009 | Supranowicz | |
| D599,032 S | 8/2009 | Bucholtz et al. | |
| D599,655 S | 9/2009 | Friebe et al. | |
| D608,011 S | 1/2010 | Giraud et al. | |
| D621,951 S | 8/2010 | Bucholtz et al. | |
| D631,168 S | 1/2011 | Bucholtz et al. | |
| D644,336 S | 8/2011 | Belfance et al. | |
| D644,337 S | 8/2011 | Belfance et al. | |
| D644,739 S | 9/2011 | Belfance et al. | |
| D644,740 S | 9/2011 | John et al. | |
| D647,211 S | 10/2011 | Belfance et al. | |
| D649,658 S | 11/2011 | Belfance et al. | |
| D649,659 S | 11/2011 | Belfance et al. | |
| 8,051,998 B1 | 11/2011 | Giraud et al. | |
| 8,474,610 B1 * | 7/2013 | Knight et al. | 206/204 |
| 2005/0118071 A1 * | 6/2005 | Sacherer | 422/100 |
| 2006/0144733 A1 | 7/2006 | Wu et al. | |
| 2006/0219578 A1 * | 10/2006 | Owensby | 206/204 |
| 2006/0219727 A1 | 10/2006 | Giraud | |
| 2008/0035658 A1 | 2/2008 | Caulfield et al. | |
| 2011/0089187 A1 | 4/2011 | Steiger et al. | |
| 2012/0055946 A1 | 3/2012 | Caulfield et al. | |
| 2012/0055947 A1 | 3/2012 | Caulfield et al. | |

FOREIGN PATENT DOCUMENTS

| | | |
|---|---|---|
| JP | 54-130974 | 9/1979 |
| JP | 2000-079973 | 3/2000 |
| JP | 2002-274576 | 9/2002 |
| WO | DM/067982 | 8/2008 |

OTHER PUBLICATIONS

Office Action issued Oct. 10, 2012 in related Design U.S. Appl. No. 29/417,148 (13 pages).

Office Action issued Oct. 12, 2012 in related Design U.S. Appl. No. 29/417,144 (13 pages).

U.S. Appl. No. 29/417,144, filed Mar. 30, 2012, Kiyoshi Wada, Toppan Printing Co., Ltd.

U.S. Appl. No. 29/417,148, filed Mar. 30, 2012, Kiyoshi Wada, Toppan Printing Co., Ltd.

PCT Written Opinion (PCT/ISA/237) issued Jun. 19, 2012 in corresponding Japanese PCT Patent Application No. PCT/JP2012/001586 (3 pages) 1 page English translation).

PCT Search Report (PCT/ISA/210) issued Jun. 19, 2012 in corresponding Japanese PCT Patent Application No. PCT/JP2012/001586 (2 pages).

* cited by examiner

F I G. 1 5
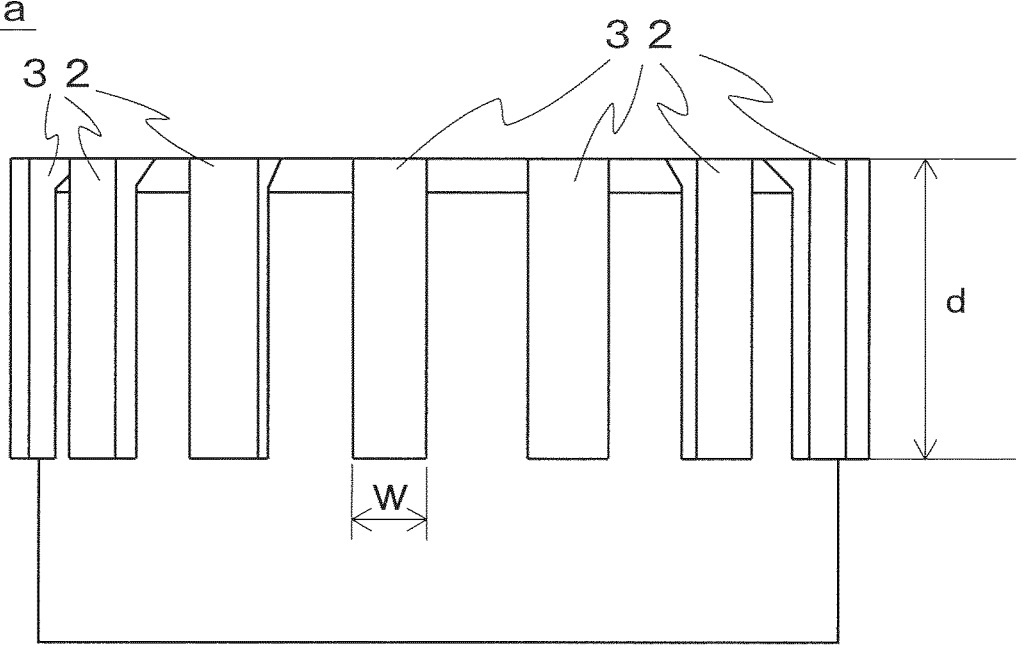

FIG. 20

| THE NUMBER OF SLITS | WATER ABSORBING CAPABILITY (mg/hr) | RATIO RELATIVE TO FIVE SLITS |
|---|---|---|
| FIVE SLITS | 1.73 | 1.00 |
| EIGHT SLITS | 2.14 | 1.24 |
| TEN SLITS | 2.47 | 1.43 |
| FIFTEEN SLITS | 3.1 | 1.79 |

MOISTURE-PROOF CONTAINER

TECHNICAL FIELD

The present invention relates to moisture-proof containers having desiccant provided therein.

BACKGROUND ART

Test pieces (detection sensor chips) used for analyzing blood or urine easily deteriorate due to moisture (water), resulting in deterioration of detection capability. Therefore, containers having desiccant provided therein are used for storing such test pieces. For example, a moisture-proof container in which a case that is formed into a cup shape, that contains desiccant therein, and that has an opening sealed with a dustproof sheet is secured to the bottom portion of the container has been suggested (Patent Literature 1). A drawback of such a moisture-proof container is that the dustproof sheet is broken due to contact with the test piece, and the desiccant that spills through the broken portion may pollute the test pieces.

CITATION LIST

Patent Literature

Patent Literature 1: Japanese Laid-Open Patent Publication No. 2002-274576

SUMMARY OF THE INVENTION

Problems to be Solved by the Invention

An object of the present invention is to make available a moisture-proof container that is excellent in moisture-proof effect, and enables remarkable reduction of pollution of contained objects (test pieces) due to desiccant.

Solution to the Problems

The inventor of the present invention has completed the present invention and has found that the above-mentioned problem can be overcome by the moisture-proof container having the following features.

Namely, the present invention is directed to

[1]: a moisture-proof container including: a container body; a lid for hermetically closing the container body so as to be openable and closable; and a desiccant storage case that has a tubular shape and that is put on a bottom portion of the container body, in which the desiccant storage case includes: an inner case having an opening at one end; a desiccant stored in the inner case; and a moisture transmission dustproof sheet for sealing the opening of the inner case, the inner case has, at an outer circumferential wall thereof, a groove connecting between an open end and a bottom portion, the container body includes a base on an inner wall of a bottom plate, and the desiccant storage case is put in the container body such that the moisture transmission dustproof sheet abuts the base, and a gap is formed between the bottom plate of the container body, and the moisture transmission dustproof sheet.

Preferably, the moisture-proof container described in [1] further includes a projection that is positioned between a plane including an outer surface of the bottom portion of the inner case and an opening of the container body, and that projects from an inner circumferential wall of the container body, such that the desiccant storage case is prevented from moving toward the opening of the container body.

The present invention is further directed to a method for producing the moisture-proof container described in [1], and the method including the steps of:

filling the inner case with the desiccant by using a filling nozzle, producing the desiccant storage case by sealing, with the moisture transmission dustproof sheet, the opening of the inner case that contains the desiccant; and putting the desiccant storage case in the container body such that the moisture transmission dustproof sheet faces the bottom portion of the container body.

Advantageous Effects of the invention

The moisture-proof container according to the present invention is excellent in moisture-proof effect and can remarkably reduce pollution of a contained object due to a desiccant.

BRIEF DESCRIPTION OF THE DRAWINGS

FIG. 15 is a front view of an inner case according to the second embodiment.

FIG. 20 illustrates moisture absorbing capability depending on the number of projections.

DESCRIPTION OF EMBODIMENTS (First Embodiment)

Figure 1:
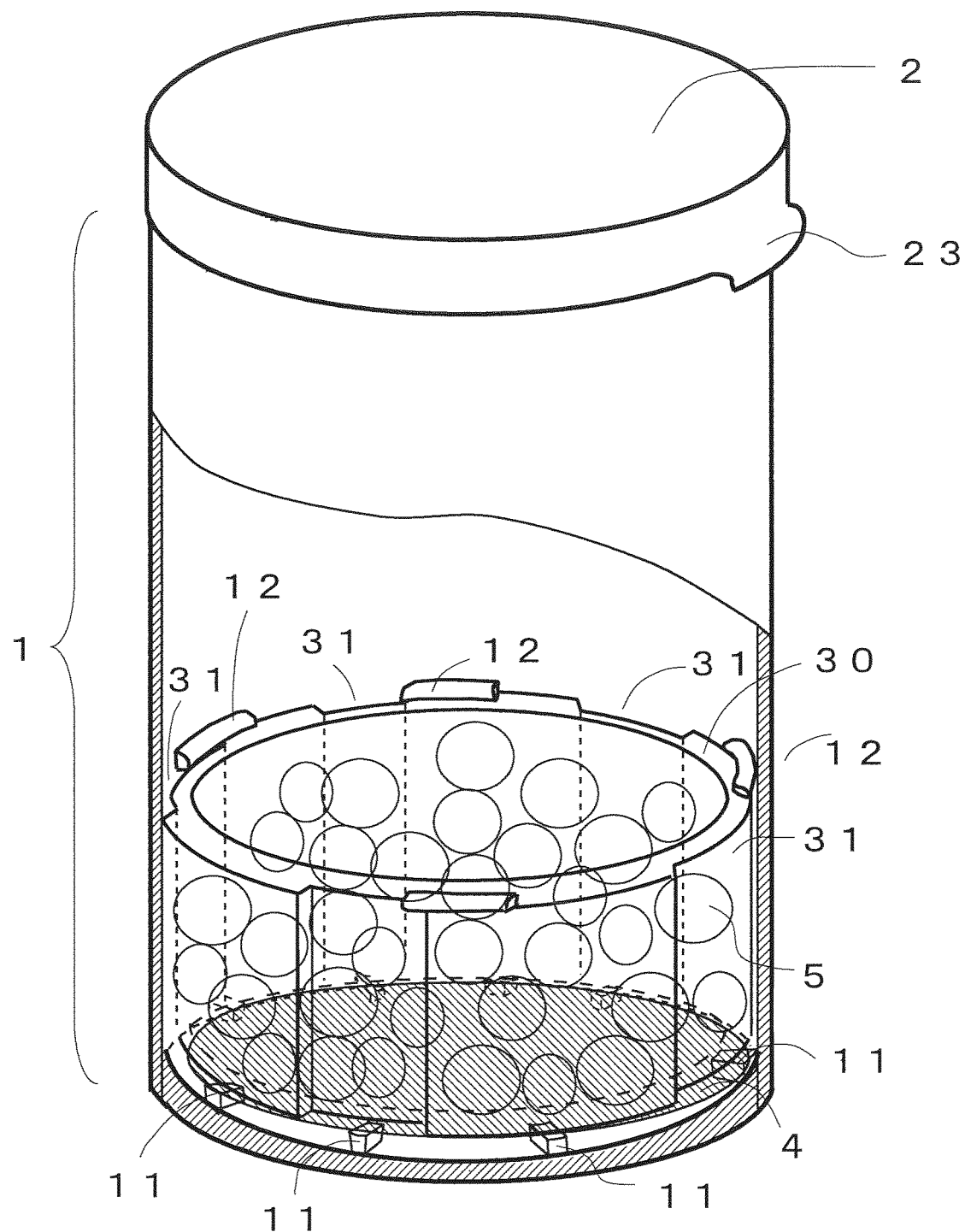
FIG. 1 is a perspective view of a moisture-proof container according to a first embodiment.
Figure 2:
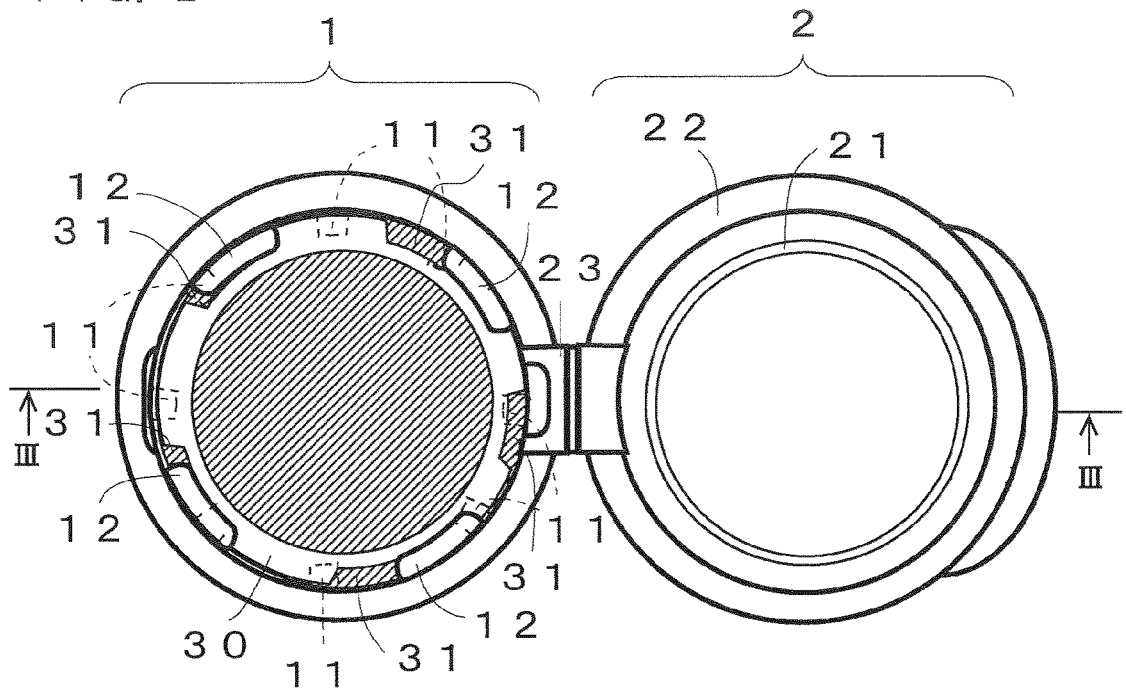
FIG. 2 is a top view of the moisture-proof container in an opened state according to the first embodiment.

FIG. 1 is a perspective view of an exemplary moisture-proof container according to a first embodiment of the present invention. FIG. 2 is a top view of the moisture-proof container, shown in FIG. 1, in an opened state, and FIG. 3 is a cross-sectional view taken along a line III-III shown in FIG. 2.

The moisture-proof container of the present invention is formed of, for example, a resin (for example, polypropylene) having a moisture-proof property. A container body 1 has a tubular shape, and has one end sealed with a bottom plate 13, and the other end opened. Examples of the tubular shape may include a cylindrical shape and prismatic shapes (such as a quadrangular-prism-shape, and a hexagonal-prism-shape).

Figure 3:
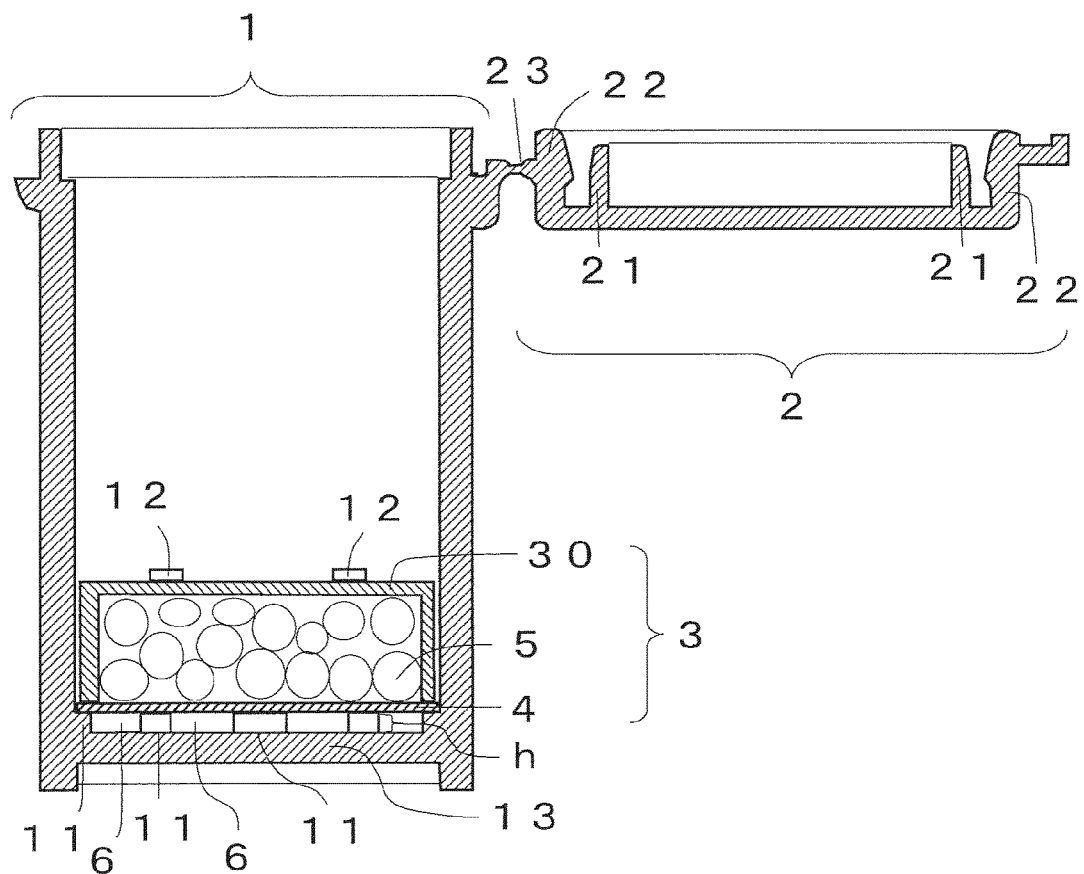
FIG. 3 is a cross-sectional view of the moisture-proof container according to the first embodiment.
Figure 4:
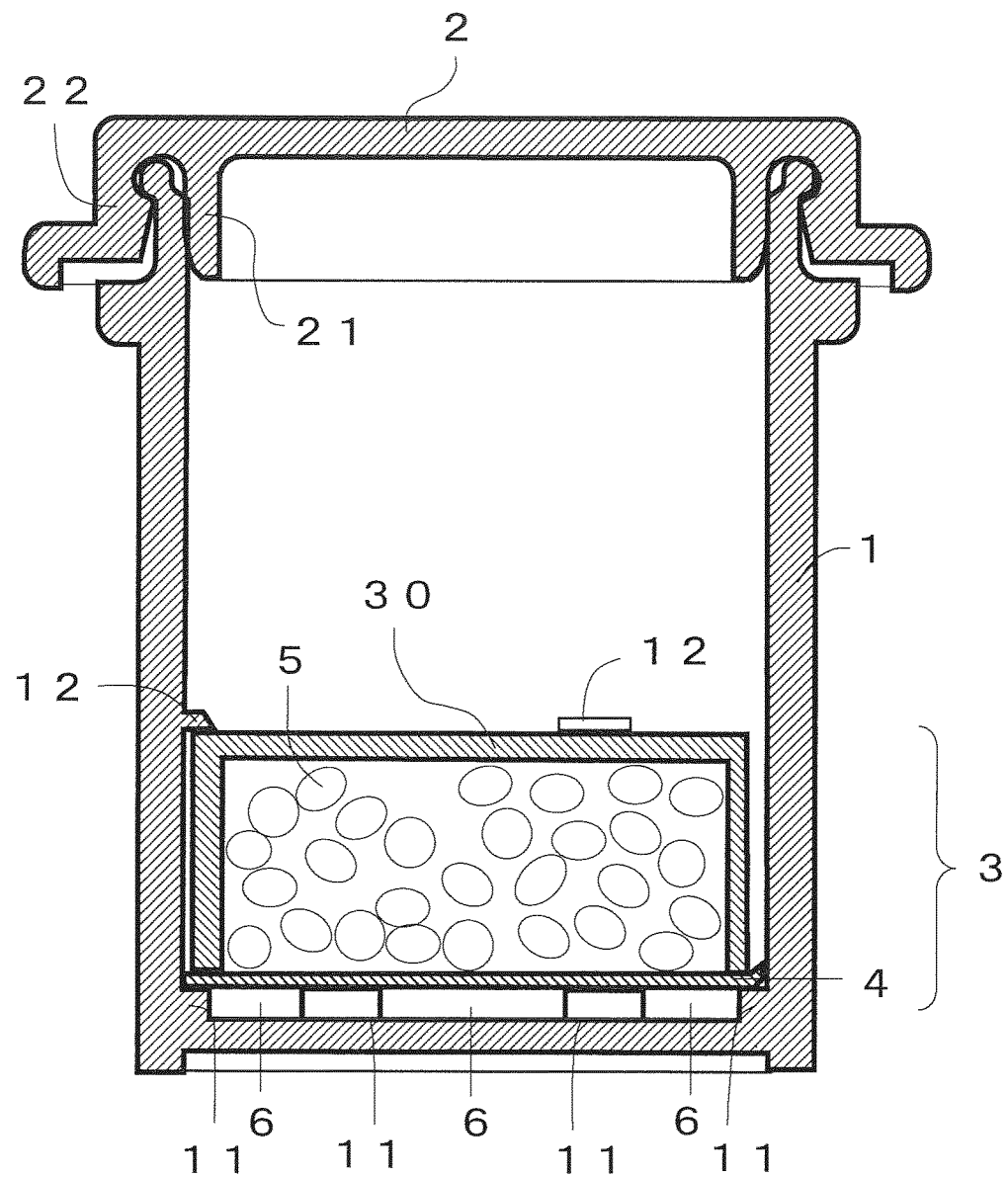
FIG. 4 is a cross-sectional view of another exemplary moisture-proof container according to the first embodiment.

When, like the moisture-proof container shown in FIG. 1 to FIG. 3, the container body 1 and a lid 2 are connected to each other via a hinge 23 to be integrally formed, the moisture-proof container can be efficiently produced as an integrally formed resin product. However, the container body 1 and the lid 2 may be separable from each other as shown in FIG. 4.

A method for sealing an opening of the container body 1 so as to be openable and closable is not limited to any specific one. For example, the container body 1 and the lid 2 are each formed as a separate component, and the lid 2 may be screwed onto the opening of the container body 1, thereby sealing the opening so as to be openable and closable.

The container body 1 has bases 11 provided in a circumferential portion of the top surface of the bottom plate 13. The bases 11 support a desiccant storage case 3 described below, and function to assuredly provide a gap 6 between the desiccant storage case 3 and the bottom plate 13. Therefore, an occupancy of the bases 11 on the bottom plate 13 is preferably small. In FIG. 1 to FIG. 4, an exemplary state in which the bases 11 are positioned along an inner circumferential wall of the container body 1 is shown. However, the positions of the bases 11 are not limited to any specific positions, and may be any positions at which the bases 11 can stably support the desiccant storage case 3. The number of the bases 11 and the shape of each base 11 are not limited to any specific ones when the desiccant storage case 3 can be stably supported. For example, a rib that radially extends from the center of the bottom plate 13 toward the inner circumferential wall of the container body 1 may be formed as the bases 11.

[Desiccant Storage Case]

The moisture-proof container according to the first embodiment of the present invention has the desiccant storage case 3 that is put on the bottom portion of the container body 1.

The desiccant storage case 3 includes an inner case 30, a desiccant 5 contained in the inner case 30, and a moisture transmission dustproof sheet 4 for sealing the opening of the inner case 30.

The inner case 30 has a tubular shape, and has one end sealed with a bottom plate, and the other end opened. The outer circumferential shape and the size of the inner case 30 are determined such that the inner case 30 can be put into the container body 1, and the outer diameter of the inner case 30 matches the inner diameter of the container body 1. However, this may not be applied to a portion in which grooves 31 described below are formed.

Figure 5:
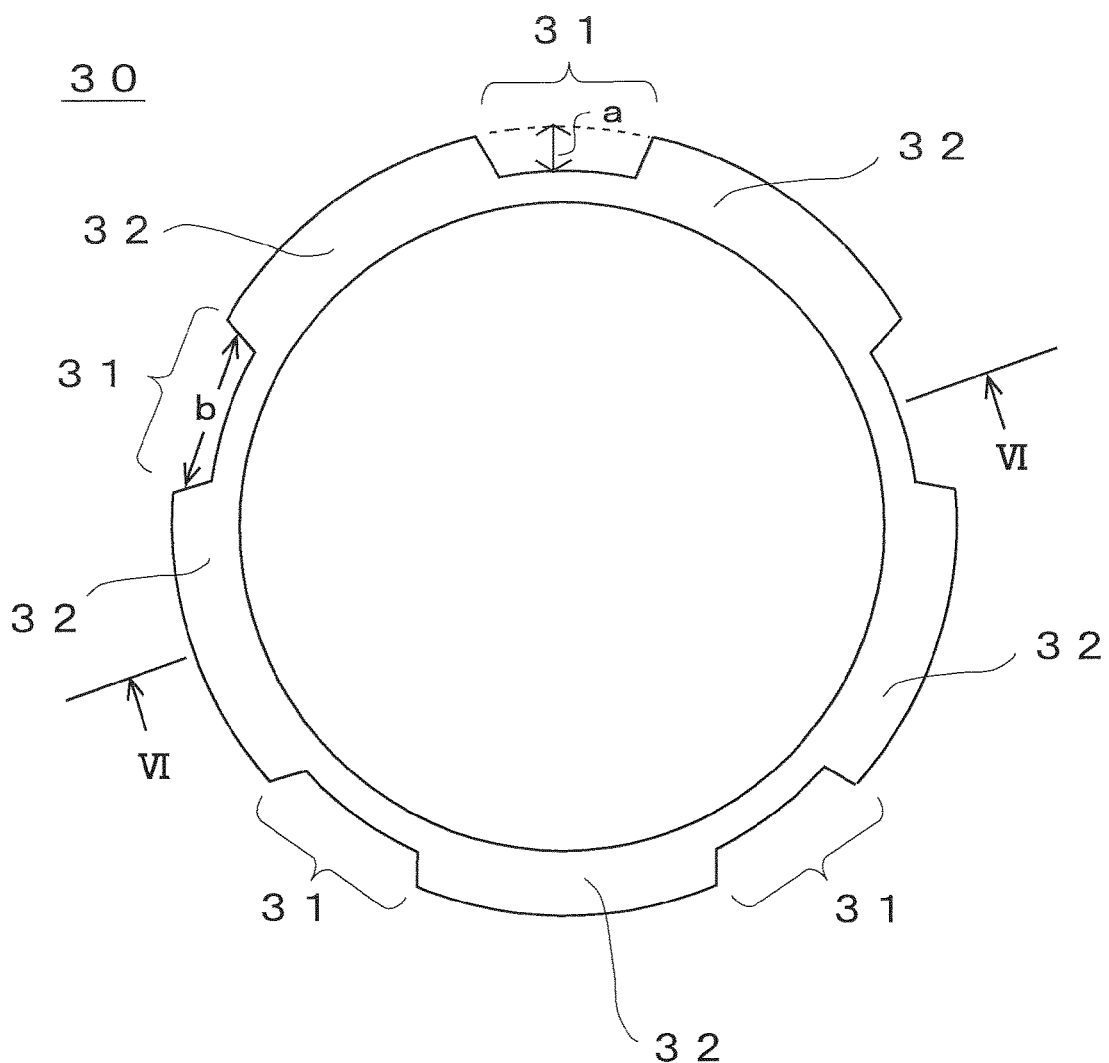
FIG. 5 is a top view of an inner case.
Figure 6:
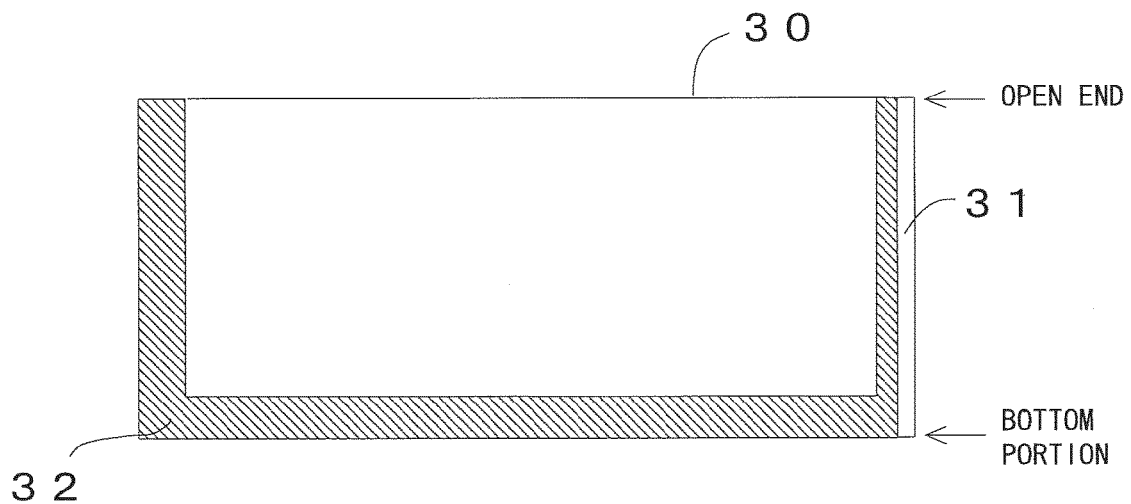
FIG. 6 is a cross-sectional view of a first exemplary inner case.

FIG. 5 is a top view of an example of the inner case 30. FIG. 6 is a cross-sectional view of the inner case 30 shown in FIG. 5 as taken along a VI-VI direction.

The grooves 31 connecting between an open end and a bottom portion of the inner case 30 are formed on the outer circumferential wall of the inner case 30. Further, the outer circumferential wall of the inner case 30 has projections 32 formed such that the outer diameter of the projections matches the inner diameter of the container body 1. In FIG. 5, the number of the grooves 31 formed in the inner case 30 is five. However, the number of the grooves 31 may be one, and the number thereof is not limited to any specific number. The grooves 31 each of which forms a straight line connecting between the open end and the bottom portion by a minimal distance are shown. However, the shape of each groove 31 is not limited to any specific one, and may be any shape that connects from the open end to the bottom portion in a continuous manner.

A depth a and a width b of each groove 31 are determined as necessary in consideration of the drying capability of the moisture-proof container described below. The number of the grooves 31 is also determined as necessary in consideration of the drying capability of the moisture-proof container.

Figure 7:
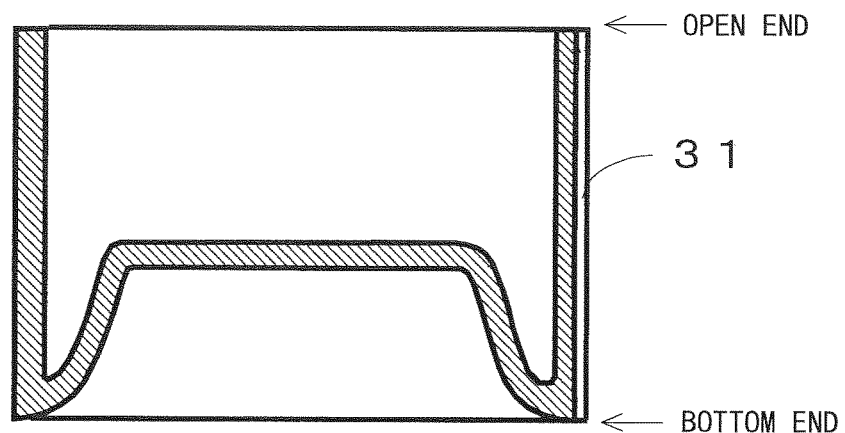
FIG. 7 is a cross-sectional view of a second exemplary inner case.

The bottom plate of the inner case 30 may be planar as shown in FIG. 6. Further, the bottom plate of the inner case 30 may be recessed such that the center portion thereof is recessed inwardly as shown in FIG. 7. The action and effect obtained by using the bottom plate shown in FIG. 7 will be described below.

The desiccant 5 is not limited to any specific desiccant, and may be any well-known or conventionally used desiccant which does not pollute or erode an contained object. Specific examples of the desiccant include chemical desiccants such as calcium oxide, calcium chloride, aluminum oxide, and iron powders, and physical desiccants such as aluminum oxide, zeolites, molecular sieves, and silica gel.

By selecting a type of the desiccant, a humidity in the moisture-proof container can be adjusted. When a zeolite and/or molecular sieve are used, a humidity in the moisture-proof container can become less than or equal to 5%. When calcium oxide, calcium chloride, or the like is used, a humidity in the moisture-proof container can become about 5 to 10%. When silica gel or aluminum oxide is used, the humidity in the moisture-proof container can become about 10% in many cases.

In the present invention, in light of preventing aggregation of the desiccant due to moisture absorption, and generation of dust due to friction and the like, a physical desiccant is preferably used. Among them, a molecular sieve can be preferably used in particular because the humidity in the moisture-proof container can be maintained low, and a drying efficiency is unlikely to be changed and water is unlikely to be released back if temperature changes.

As the moisture transmission dustproof sheet 4, any sheet that has a moisture transmission property and a dustproof property, and that has a uniform strength, can be used. Specific examples of the moisture transmission dustproof sheet 4 include non-woven fabrics formed of resins such as a polyethylene and a polypropylene, microporous films, and microporous sheets. Examples of such a sheet, which is commercially available, include a product of US DuPont; "Tyvek (registered trademark)", a product of Sekisui Plastics Co., Ltd.; "Cell-pore", a product of Tokuyama Soda Co., Ltd.; "NF SHEET", and a product of NITTO DENKO CORPORATION; "NITOFLON (registered trademark)".

The desiccant 5 is put and stored in the inner case 30, and the opening of the inner case 30 is sealed with the moisture transmission dustproof sheet 4, to produce the desiccant storage case 3.

Figure 8:
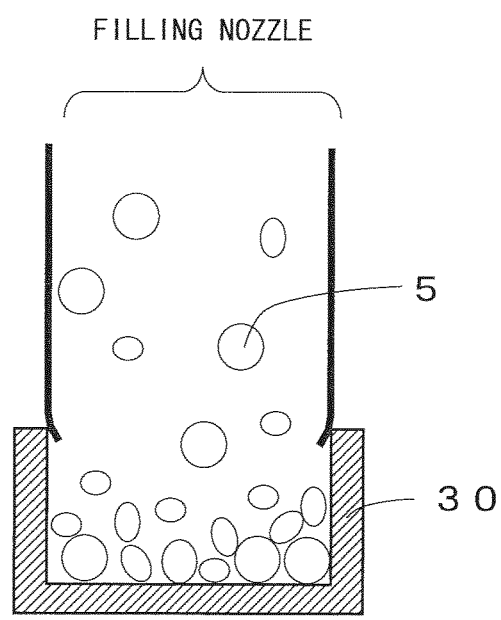
FIG. 8 illustrates a moisture-proof container production method.

When the desiccant 5 is put and stored in the inner case 30, for example, use of a filling nozzle as shown in FIG. 8 enables a storage operation to be efficiently performed.

After the desiccant 5 is stored, the opening of the inner case 30 is sealed with the moisture transmission dustproof sheet 4. The moisture transmission dustproof sheet 4 is cut in advance so as to have a shape and a size that matches the opening of the inner case 30. The moisture transmission dustproof sheet 4 having been cut can be aligned with the opening of the inner case 30 by utilizing a suction arm using air suction.

Figure 9:
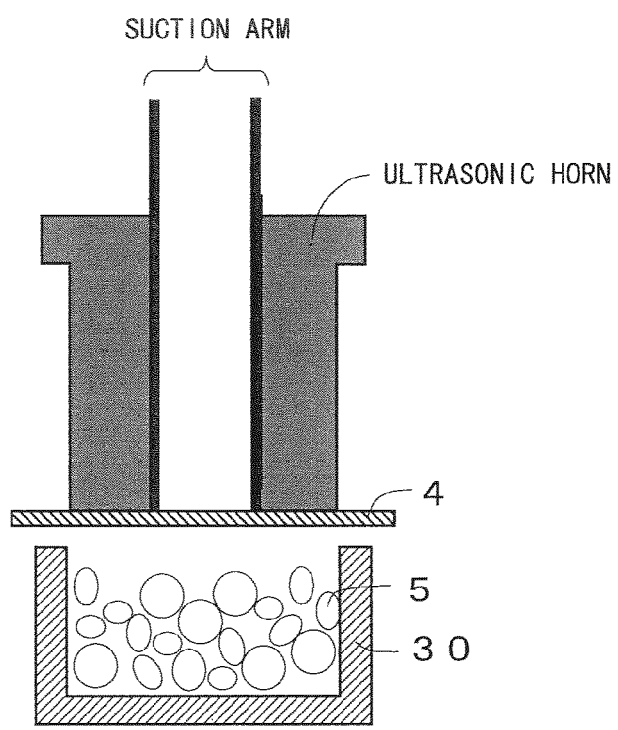
FIG. 9 illustrates a moisture-proof container production method.

A method for sealing the opening of the inner case 30 with the moisture transmission dustproof sheet 4 is not limited to any specific one. Examples of the method include a welding using an ultrasonic wave. As shown in FIG. 9, the moisture transmission dustproof sheet can be heated and welded by using an ultrasonic horn while the moisture transmission dustproof sheet is being held by using the suction arm. An area in which the moisture transmission dustproof sheet 4 is welded onto the opening of the inner case 30 is preferably reduced to the extent that an adhesion therebetween does not become poor. A great area for the welding may cause crinkles or warping to be generated in the moisture transmission dustproof sheet 4 when the inner case 30 is put into the container body 1, which is unfavorable.

Figure 10:
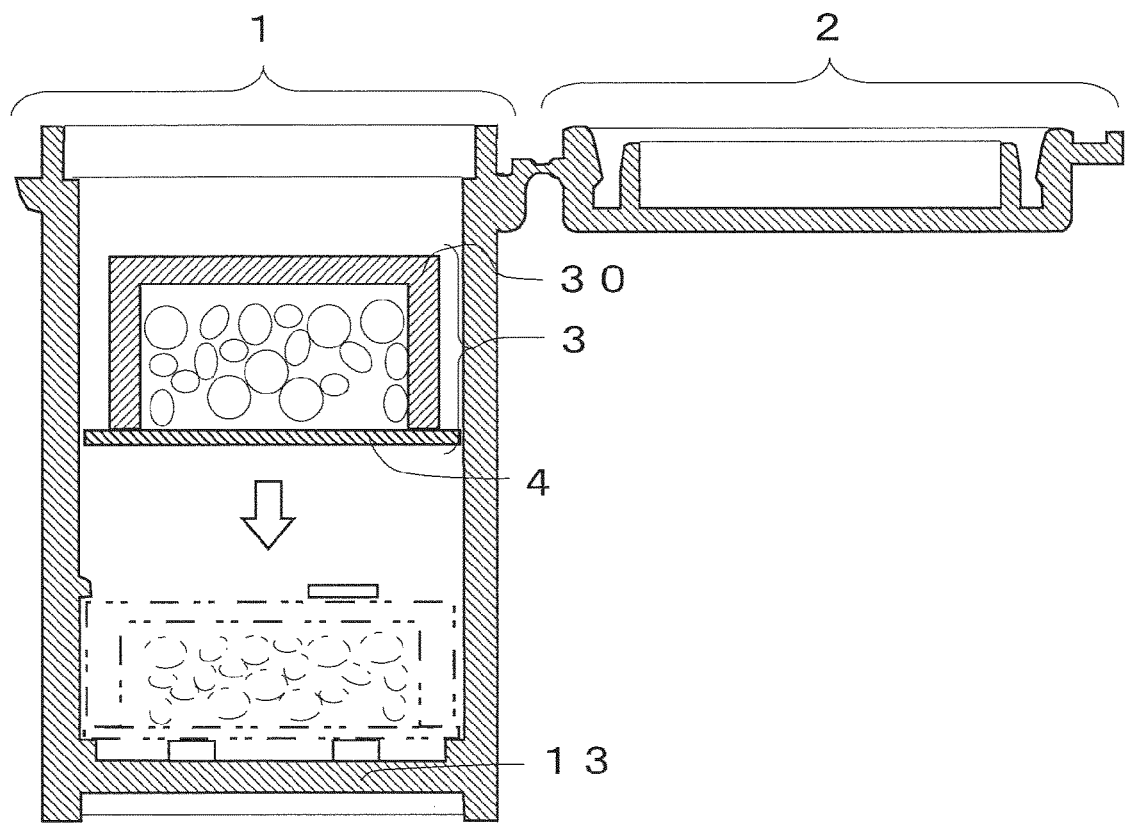
FIG. 10 illustrates a moisture-proof container production method.

The desiccant storage case 3 having been obtained as described above is put into the container body 1. As shown in FIG. 10, the desiccant storage case 3 is put such that the moisture transmission dustproof sheet 4 faces the bottom plate 13 of the container body 1. In other words, the opening of the inner case 30 is set so as to face the bottom plate 13 of the container body 1, and the bottom of the inner case 30 is set so as to face the opening side of the container body 1. The desiccant storage case 3 is put such that the moisture transmission dustproof sheet 4 abuts the bases 11 provided on the inner wall of the bottom plate 13 of the container body 1.

Positions at which the bases 11 are provided and the sizes of the bases 11 are appropriately adjusted, and immediately after the ultrasonic welding process step as shown in FIG. 9 is performed, the desiccant storage case 3 is put into the container body 1, and the welding between the moisture transmission dustproof sheet 4 of the desiccant storage case 3 and the bases 11 of the container body 1 can be performed.

After the desiccant storage case 3 is stored in the container body 1, the opening of the container body 1 is hermetically closed by the lid 2, so that a dry state in the container body 1 is enabled, thereby completing the moisture-proof container of the present invention.

In the moisture-proof container according to the first embodiment of the present invention, the moisture transmission dustproof sheet 4 that functions as a path through which moisture (water) in the moisture-proof container reaches the desiccant 5 is provided so as to face the bottom plate 13 of the container body 1. However, the bases 11 are provided on the inner wall of the bottom plate 13, so that the gap 6 is formed between the bottom plate 13 and the moisture transmission dustproof sheet 4. Further, the grooves 31 are formed on the outer circumferential wall of the inner case 30. Therefore, the moisture (water) in the moisture-proof container passes through a space between the grooves 31 and the inner circumferential wall of the container body 1, to move into the gap 6. The moisture (water) having moved into the gap 6 is transmitted through the moisture transmission dustproof sheet 4, and adsorbed by the desiccant 5.

On the other hand, the inner case 30 contacts with the contained object on the bottom portion of the inner case 30. The bottom portion is tough as compared to the moisture transmission dustproof sheet 4, and a possibility that dust of the inner case 30 is generated due to the contact with the contained object (test piece) is extremely low. Further, a concern that injury or the like occurs in the desiccant storage case 3, and the desiccant 5 and dust thereof spill externally from the desiccant storage case 3 due to the injury, is remarkably reduced. Namely, the moisture-proof container according to the first embodiment of the present invention is a moisture-proof container excellent in that a concern that a contained object is polluted due to dust generated by the moisture-proof container itself being broken, the desiccant 5, and dust thereof, is remarkably reduced.

As described above, the moisture-proof container according to the first embodiment of the present invention has a stable drying capability while restricts the contained object from being polluted due to the desiccant 5.

Although the drying capability of the moisture-proof container can be adjusted by selection of types of the desiccant 5 as described above, the drying capability can be also adjusted by selection of a depth a and a width b of each groove 31, and the number of the grooves 31. Further, the drying capability can be adjusted by selection of a height h of each base 11, and an area of a surface on which contact with the moisture transmission dustproof sheet 4 occurs.

When the depth a and the width b of each groove 31 are increased, and the number of the grooves 31 is increased, a great amount of moisture (water) can be absorbed in a short time period, so that the moisture-proof container can become excellent in that an effect can be immediately obtained. However, the drying capability of the desiccant 5 becomes diminished in a short time period, and the lifespan of the moisture-proof container is shortened.

Increase of the height h of each base 11 leads to increase of a space of the gap 6, so that the moisture-proof container can become excellent in that an effect can be immediately obtained.

When an area of a surface on which the bases 11 contact with the moisture transmission dustproof sheet 4 is increased, an area in which moisture (water) is transmitted is reduced, so that the drying is gradually performed. Therefore, while the moisture-proof container is poor in that an effect cannot be immediately obtained, the lifespan thereof is increased.

Further, the moisture-proof container according to the first embodiment of the present invention preferably has projections 12 on the inner circumferential wall of the container body 1. The projections 12 are positioned between the opening of the container body 1 and a plane including the outer surface of the bottom portion of the inner case. The projections 12 function so as to prevent the desiccant storage case 3 put on the bottom portion of the container body 1 from moving toward the opening of the container body 1.

The shape and the size of each projection 12 are not limited to any specific ones. However, the shape and the size thereof are selected so as not to prevent the desiccant storage case 3 from being put in the bottom portion of the container body 1.

The number of the projections 12 may be one or greater than one.

Figure 11:
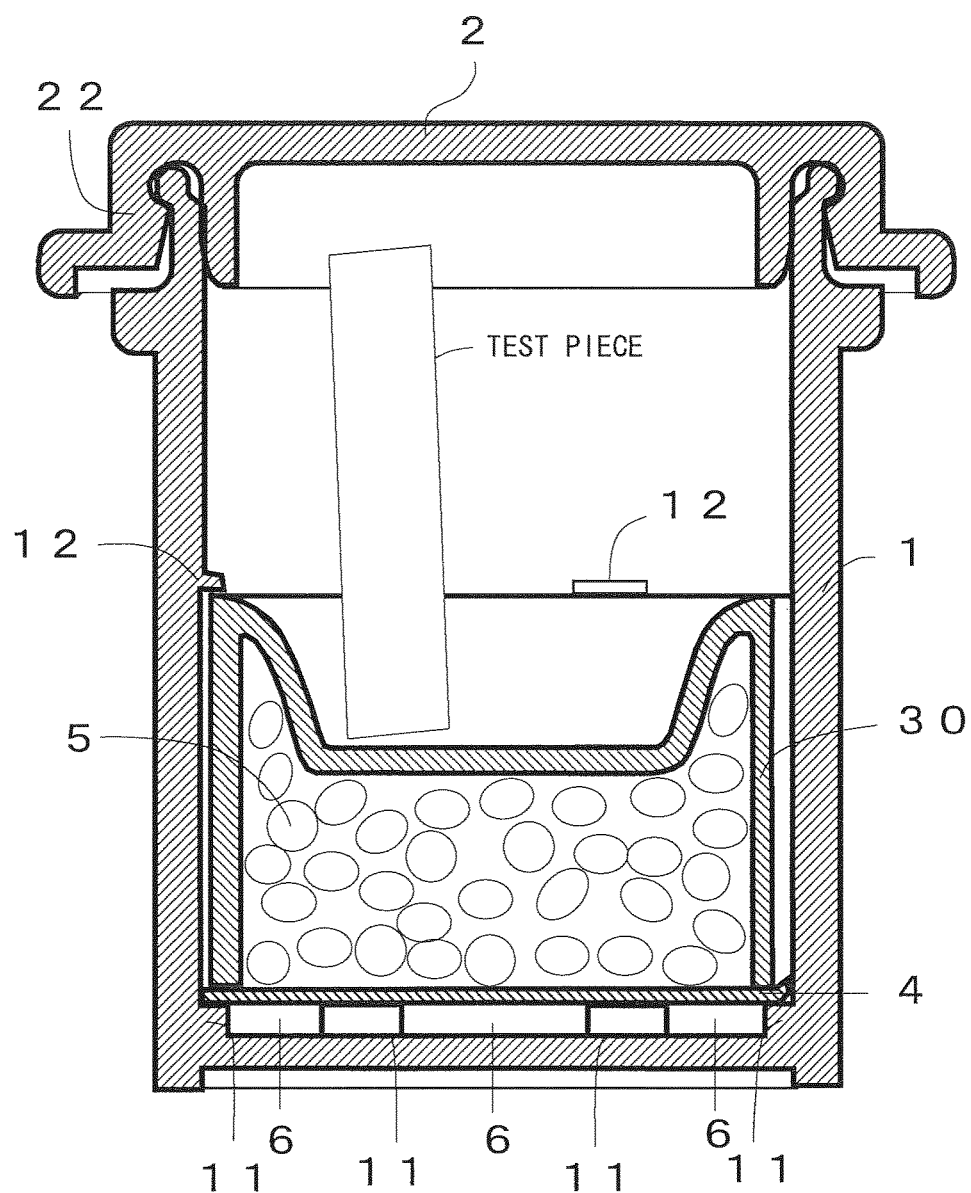
FIG. 11 is a cross-sectional view of another exemplary moisture-proof container according to the first embodiment.

FIG. 11 shows an exemplary case in which the inner case 30 shown in FIG. 7 is used for the moisture-proof container according to the first embodiment of the present invention. In order to increase an amount of the desiccant, a capacity of the desiccant storage case 3 may be increased. However, there is a problem that, in a case where the height of the container body 1 is not sufficient, if the height of the desiccant storage case 3 is merely increased, a storage space for the contained object (such as test pieces) cannot be assuredly obtained. When the moisture-proof container is structured as shown in FIG. 11, the capacity of the desiccant storage case 3 can be increased without changing the length of the container body 1, so that an amount of the desiccant 5 to be contained can be increased, and the contained objects (such as test pieces)

having a uniform length can be stored. Further, the bottom plate of the inner case 30 shown in FIG. 11 includes a tapered shape, and an inner diameter is gradually reduced from a circumferential portion. Therefore, even when the contained object is put onto the circumferential edge portion of the bottom plate, the contained object is guided into the recessed center portion, so that closing of the lid is not prevented. Therefore, the tapered shape enables the contained object to be stably stored. However, in a case where it is unnecessary to consider that the contained object is to be stably stored, at least a portion of the bottom plate may be stepped to adjust the capacity of the desiccant storage case 3.

Figure 12:
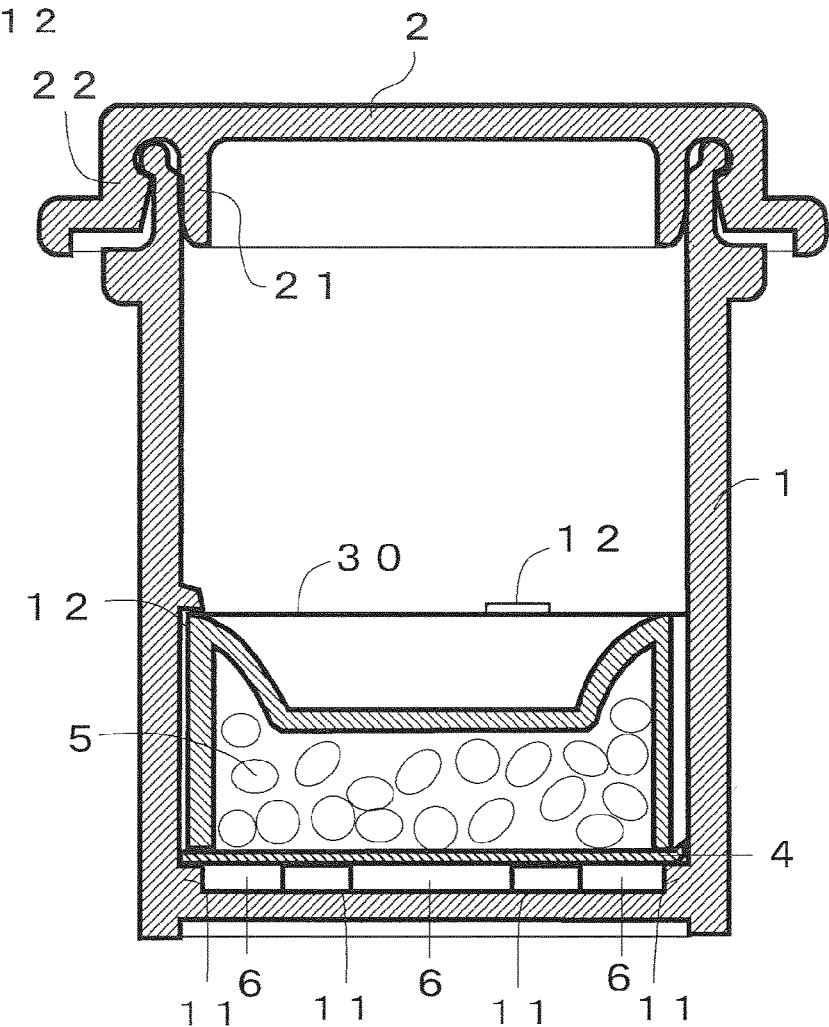
FIG. 12 is a cross-sectional view of still another exemplary moisture-proof container according to the first embodiment.

FIG. 12 shows an exemplary case in which the inner case 30 having such a shape that the bottom plate of the inner case 30 is recessed at the center of the bottom plate is adopted, similarly to the moisture-proof container shown in FIG. 11, and the capacity of the desiccant storage case 3 is reduced. An amount of the desiccant 5 to be stored can be adjusted by the height of the inner case 30 and a degree of the recess being adjusted, so that the drying capability and the lifespan of the moisture-proof container can be set as desired.

(Second Embodiment)

Figure 13:
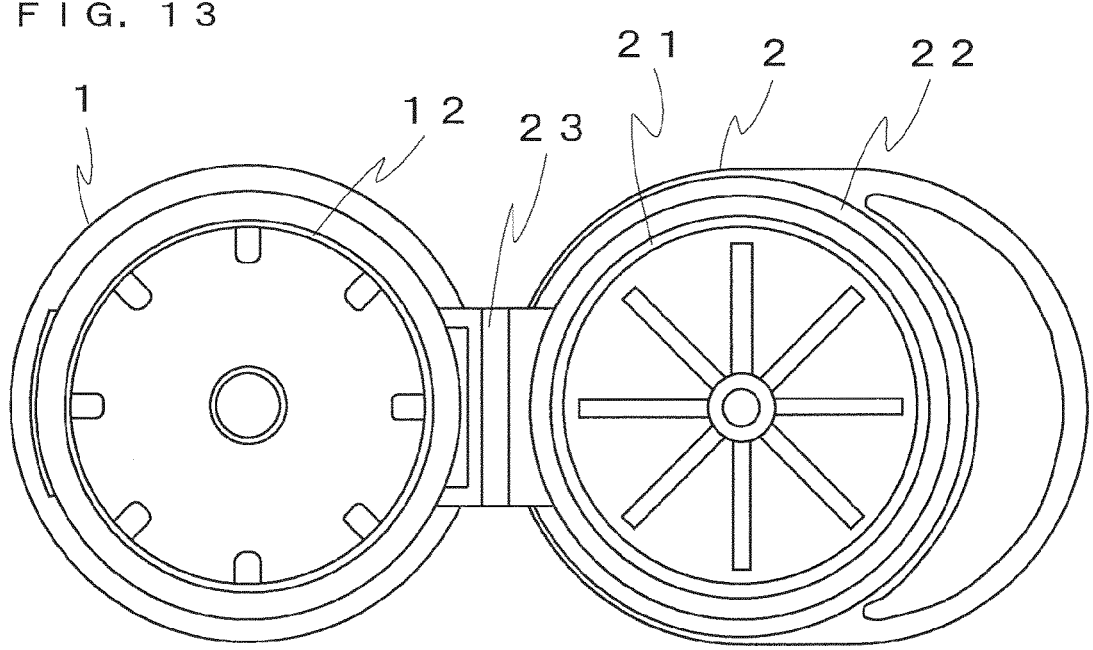
FIG. 13 is a top view of a moisture-proof container in an opened state according to a second embodiment.
Figure 14:
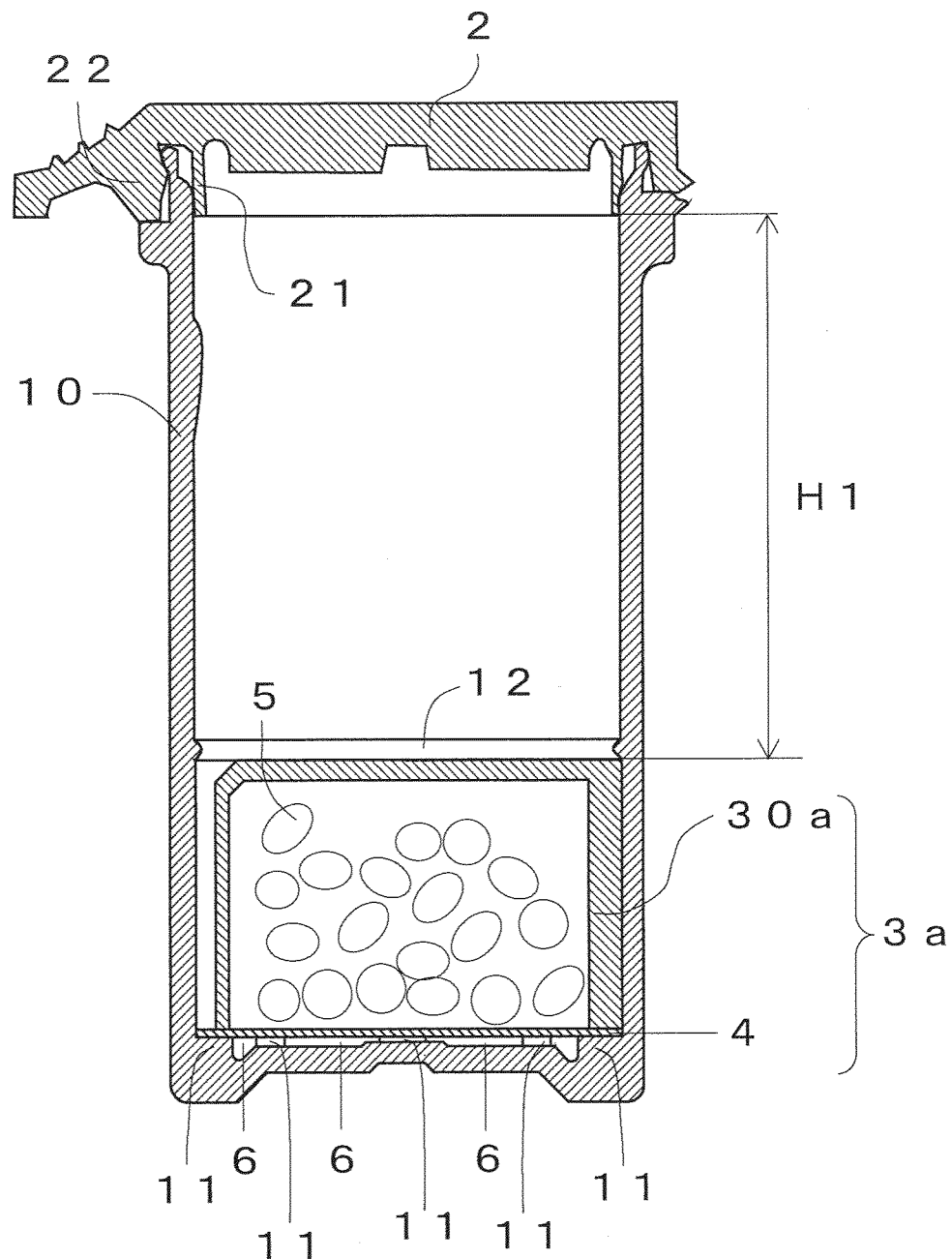
FIG. 14 is a cross-sectional view of a closed state according to the second embodiment.

FIG. 13 is a top view of a moisture-proof container in an opened state according to a second embodiment, and FIG. 14 is a cross-sectional view of the moisture-proof container in a closed state according to the second embodiment. The same components as used for the moisture-proof container of the first embodiment are denoted by the same corresponding reference numerals, and detailed description thereof is not given. The present embodiment is different from the first embodiment in that the projection 12 is provided on the entire circumference of the inner wall of the container body 10, and a portion of a corner of the bottom portion of an inner case 30*a* is chamfered in the present embodiment. When the projection 12 is provided on the entire circumference of the inner wall of the container body 10, a desiccant storage case 3*a* put on the bottom portion of the container body 10 is assuredly prevented from moving toward the opening of the container body 10. Further, when the projection 12 is provided on the entire circumference of the inner wall of the container body 10, a smooth flow of air in the moisture-proof container toward the gap 6 is restrained. However, when a portion of a corner of the bottom portion at which the grooves 31 of the inner case 30*a* are formed, is chamfered, a state in which smooth flow of the air is restrained as described above can be prevented.

Figure 16:
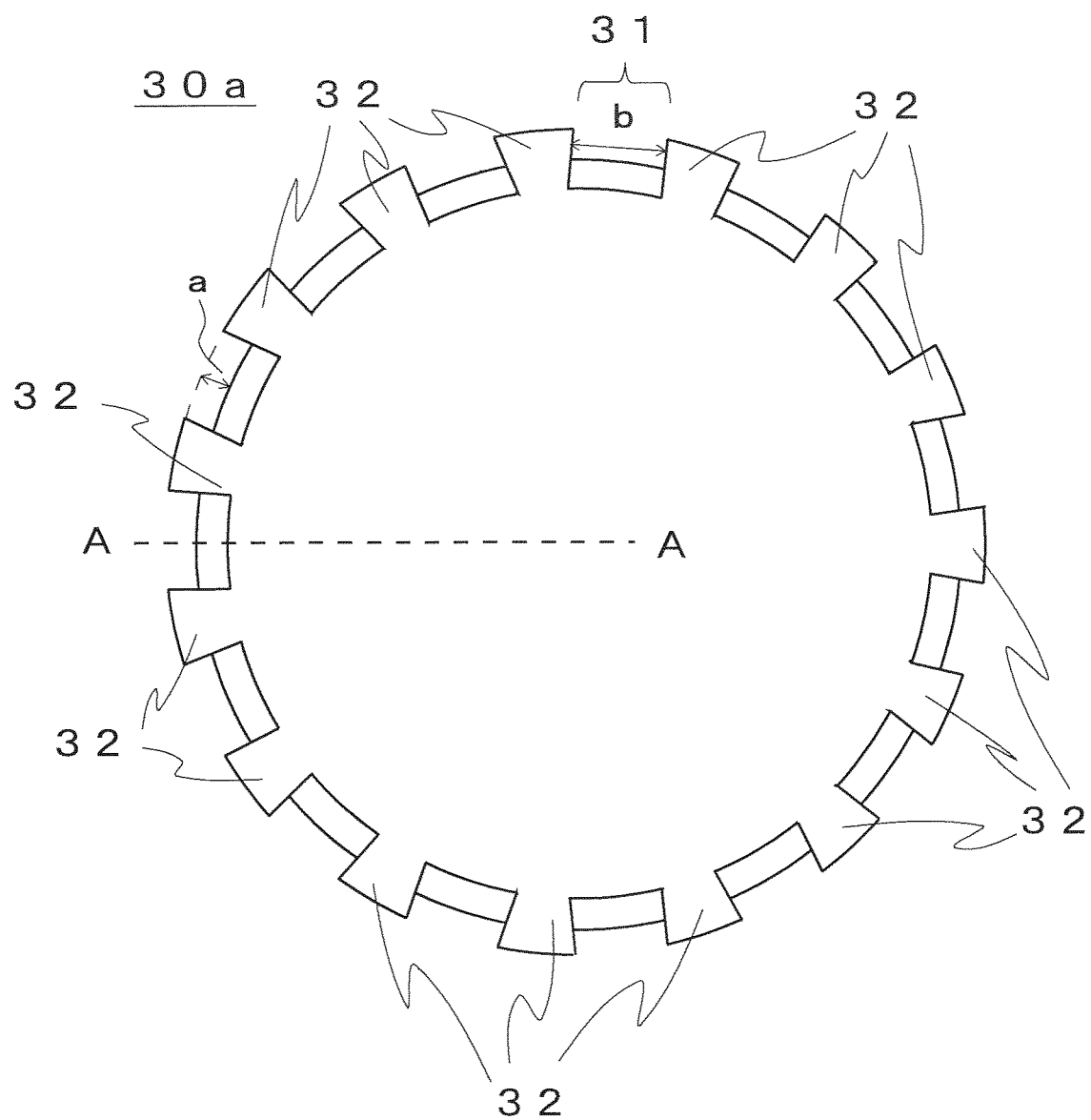
FIG. 16 is a top view of the inner case according to the second embodiment.

FIG. 15 is a front view of the inner case 30*a* of the desiccant storage case 3 of the second embodiment. FIG. 16 is a top view of the inner case 30*a*. The outer circumferential wall of the inner case 30*a* includes a plurality of projections 32 having an outer diameter that matches the inner diameter of the container body 10. Although the number of the projections 32 is 16 in FIG. 15, the number of the projections 32 is not limited to any specific number when the desiccant storage case 3 can be prevented from moving from the projection 12 toward the opening of the container body 10. Further, the projections 32 may not be provided on the entire circumference of the outer wall. However, the number of the projections 32 preferably ranges from 2 to 30 in light of conditions for designing a mold, and for preventing the desiccant storage case 3 from moving from the projection 12 toward the opening of the container body 10. Further, although the bottom portion of the grooves 31 is formed so as to have a plane surface, the bottom portion may be formed so as to have a curved surface.

The drying capability of the moisture-proof container can be adjusted by selection of a depth d and a width w of each projections 32, and the number of the projections 32. When the number of the projections 32 is increased, a great amount of moisture (water) can be absorbed in a short time period. Therefore, the moisture-proof container can become excellent in that an effect can be immediately obtained. However, the drying capability of the desiccant 5 becomes diminished in a short time period, and the lifespan of the moisture-proof container is shortened. It is more preferable that setting is made according to a desired water absorbing speed, which will be described below. Further, the depth a and the width b of each groove 31 are preferably determined, according to the size of the contained object, so as to prevent the contained object from being caught by the groove 31.

It is assumed that the size of the contained object is defined so as to have a longitudinal dimension e, a transverse dimension f, and a height g. In order to prevent the contained object from dropping into the groove 31, the following size needs to be satisfied. When the width b of each groove 31 is greater than the transverse dimension f of the contained object, the size may be determined such that the depth a of each groove 31 is defined so as to range from 10% of the longitudinal dimension e of the contained object to 100% thereof. Further, when the width b of each groove 31 is less than or equal to the transverse dimension f of the contained object, the size may be determined such that the depth a of each groove 31 is defined so as to range from 10% of the longitudinal dimension e of the contained object to 100% thereof, or the depth a of each groove 31 is defined so as to be less than or equal to the width b of each groove 31, and is not greater than 100% of the longitudinal dimension e of the contained object. Further, it is preferable that the width w of each projection 32 is set, as necessary, so as to satisfy the size described above. Furthermore, a height H1 from under an inner ring 21 of the lid 2 for closing the opening of the container body 10 to the bottom portion of the desiccant storage case 3*a* is preferably greater than or equal to the height g of the contained object so as to prevent the contained object from being caught between the lid 2 and the container body 10 when the opening of the container body 10 is closed by the lid 2. For example, the height H1 from under the inner ring 21 of the lid 2 for closing the opening of the container body 10 as shown in FIG. 13 to the bottom portion of the desiccant storage case 3*a* is set as, for example, 28.3 mm. In this case, the height g of the contained object is preferably less than 28.3 mm.

Figure 17:
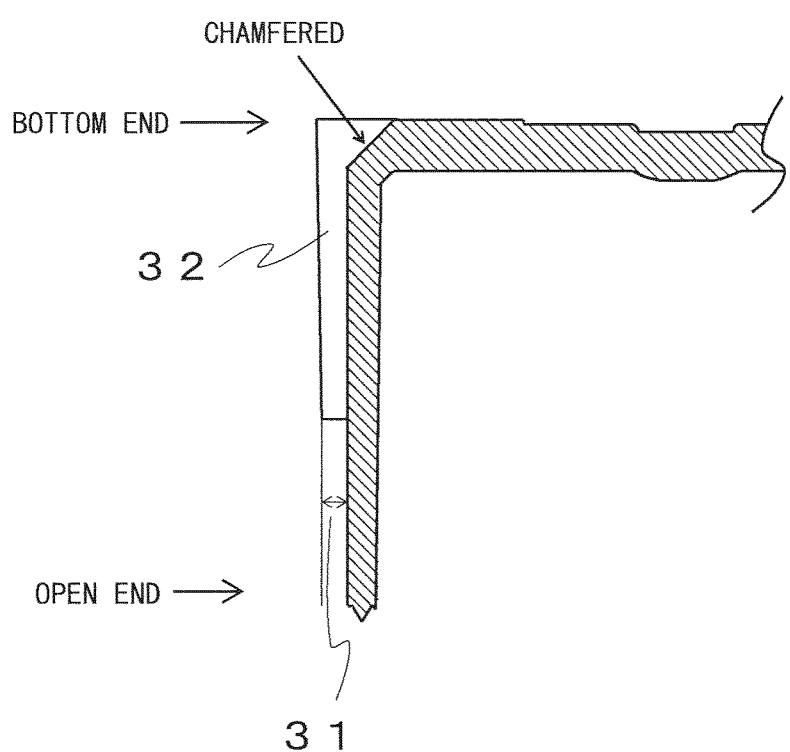
FIG. 17 is a partial cross-sectional view of the inner case according to the second embodiment.

FIG. 17 is a cross-sectional view taken along a line A-A shown in FIG. 16. In the present embodiment, a corner of the upper edge portion of the bottom portion at which the grooves 31 of the inner case 30 are formed, is diagonally cut so as to form a plane, that is, C-chamfered. By the C-chamfering, a gap between the projection 12 and the inner case 30*a* can be increased as compared to a gap between the projection 12 and the inner case 30 according to the first embodiment. Therefore, even when the projection 12 is provided on the entire circumference of the inner wall of the container body 10, a state in which a smooth flow of air in the container body 10 through the grooves 31 into the desiccant storage case 3*a* is restrained is prevented. Although the upper edge portion of the bottom portion at the grooves 31 is diagonally cut so as to form a plane, that is, C-chamfered in the present embodiment, the upper edge portion may be cut so as to form a curved surface, that is, R-chamfered.

The desiccant 5 and the moisture transmission dustproof sheet 4 to be used may be the same as those used in the first embodiment. When a filling nozzle is similarly used in order to put and store the desiccant 5 in the inner case 30*a*, the storage operation can be efficiently performed. Further, a method for sealing the opening of the inner case 30*a* with the moisture transmission dustproof sheet 4 is not limited to any specific method. For example, welding using ultrasonic wave can be selected.

Figure 18:
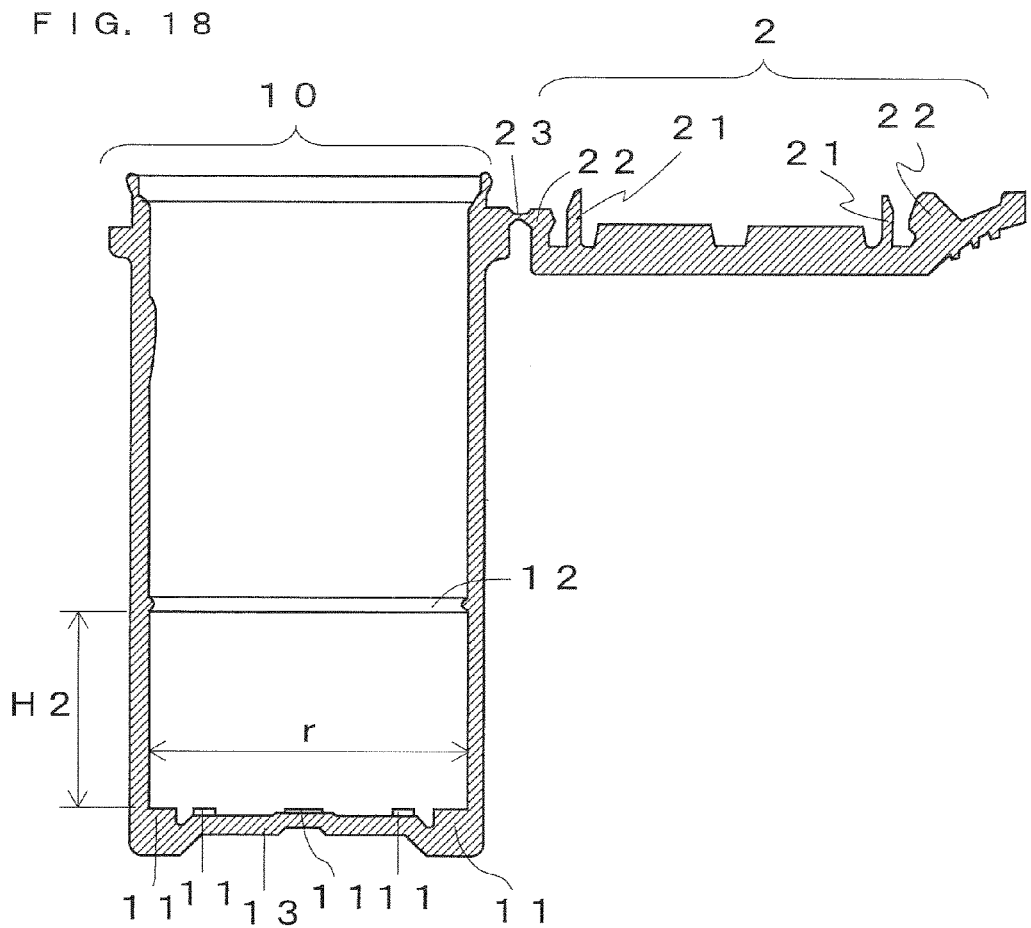
FIG. 18 is a cross-sectional view of a container body in an opened state according to the second embodiment.

FIG. 18 is a cross-sectional view of the container body 10 according to the second embodiment. The size of a space for storing the desiccant storage case 3a as shown in FIG. 18 is set such that, for example, a height H2 is 14.6 mm, and a diameter r is 22.33 mm.

In order to produce the moisture-proof container according to the second embodiment, the desiccant storage case 3a having been obtained as described above is put such that the moisture transmission dustproof sheet 4 abuts the bases 11 of the container body 10, and the contained object (such as test pieces) is stored in the container body 10, and thereafter the opening of the container body 10 is closed by the lid 2, and the container body 10 is put into a dry state.

In the moisture-proof container according to the second embodiment, the desiccant storage case 3a having been put on the bottom portion of the container body 10 can be more assuredly prevented from moving toward the opening of the container body 10 as compared to in the moisture-proof container of the first embodiment.

(Sample 1)

The desiccant storage case 3a including the desiccant 5 and the inner case 30a having five projections 32 was put into the container body 10, and a temperature and humidity meter was adhered to the reverse side of the lid 2 by using a double-sided tape. The moisture-proof container having been obtained as described above was put, with the lid 2 opened, in a constant temperature and humidity bath having been set such that the temperature was 30° C. and the humidity was 70%, and was left as it was for one hour, thereby obtaining sample 1.

(Sample 2)

The desiccant storage case 3a including the desiccant 5 and the inner case 30a having Fifteen projections 32 was put into the container body 10, and sample 2 was obtained in the same process steps as those for sample 1.

Figure 19:
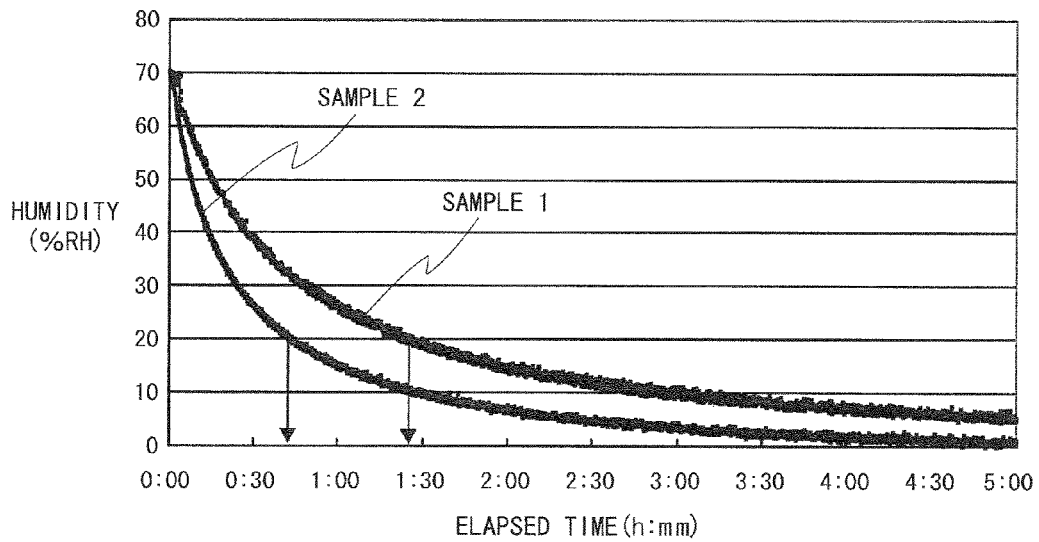
FIG. 19 illustrates a moisture absorbing capability of moisture-proof containers according to samples 1 and 2 of the second embodiment.

A moisture absorbing state was measured for each of sample 1 and sample 2 in a state where the lid 2 was closed in the constant temperature and humidity bath described above. The results are indicated in FIG. 19. FIG. 19 indicates that it took about one hour and 30 minutes to reduce, to 20%, the humidity of sample 1 having five projections 32, while it took about 45 minutes to reduce, to 20%, the humidity of sample 2 having fifteen projections 32.

Further, the desiccant storage cases 3a including the desiccant 5 and the inner cases 30a having five projections 32, eight projections 32, ten projections 32, and fifteen projections 32, respectively, were prepared, and the desiccant storage case 3a including the desiccant 5 and each of the inner cases 30a was put in the container body 10, and the weight of each moisture-proof container was measured by using a precision electronic balance. Thereafter, each moisture-proof container was put, with the lid 2 opened, in a constant temperature and humidity bath having been set such that the temperature was 30° C. and the humidity was 70%, and was left as it was for 24 hours. Then, the weight of each moisture-proof container was measured again by using an electronic balance, and a water absorbing capability per one hour was calculated, and was compared with that of the moisture-proof container having five projections 32. The results of the calculation and comparison described above are indicated in FIG. 20.

The comparison result shown in FIG. 19 and FIG. 20 indicates that a moisture absorbing speed and water absorbing capability can be set as necessary by adjustment of the number of the projections 32.

Each of the moisture-proof containers according to the first embodiment and the second embodiment of the present invention effectively protects the moisture transmission dustproof sheet 4 from strike by a contained object, and reduces pollution of the contained objects due to the desiccant 5 and dust thereof. In addition, the dehumidifying speed and the dehumidification-enabled period of the moisture-proof container can be optionally adjusted.

Industrial Applicability

The moisture-proof container according to the present invention can be variously used as a container for storing objects that easily deteriorate due to moisture and dust of a desiccant. The moisture-proof container according to the present invention can be favorably used as, for example, a container for storing test pieces used for blood sugar level tests and urine tests, and chemicals (such as tablets).

DESCRIPTION OF THE REFERENCE CHARACTERS 1, 10 container body
11 base
12 projection
13 bottom plate
2 lid
21 inner ring
22 outer ring
23 hinge
3, 3a desiccant storage case
30, 30a inner case
31 groove
32 projection
4 moisture transmission dustproof sheet
5 desiccant
6 gap

The invention claimed is:

1. A moisture-proof container comprising:
a container body having a tubular shape and an opening;
a lid for hermetically closing the container body so as to be openable and closable;
a desiccant storage case that has a tubular shape and that is put on a bottom portion of the container body,
wherein the desiccant storage case includes:
an inner case having an opening at one end for filling the inner case with a desiccant; and
a moisture transmission dustproof sheet for sealing the opening of the inner case, and
the inner case has, at an outer circumferential wall thereof, a groove connecting between the opening and a bottom portion of the inner case; and
a first projection on an inner circumferential wall of the container body for preventing the desiccant storage case from moving toward the opening of the container body,
wherein
the container body includes a base on an inner wall of a bottom plate for supporting the desiccant storage case and for providing a gap formed between the bottom plate of the container body and the moisture transmission dustproof sheet,
thereby the desiccant storage case is to be put in the container body such that the moisture transmission dustproof sheet abuts the base with the gap formed between the bottom plate of the container body and the moisture transmission dustproof sheet.

2. The moisture-proof container according to claim 1, wherein the first projection is positioned on the inner circumferential wall of the container body between a plane including an outer surface of the bottom portion of the inner case of the desiccant storage case and the opening of the container body.

3. The moisture-proof container according to claim 2, wherein the first projection is formed on an entire circumference of the inner circumferential wall of the container body, the outer circumferential wall of the inner case of the desiccant storage case has an outer diameter that matches an inner diameter of the container body, and
   a corner of the bottom portion of the inner case at which the groove is formed, is chamfered.

4. A method for producing the moisture-proof container according to claim 1, the method comprising:
   filling the inner case with the desiccant by using a filling nozzle,
   producing the desiccant storage case by sealing the opening of the inner case with the moisture transmission dustproof sheet,
   putting the desiccant storage case in the container body such that the moisture transmission dustproof sheet faces the bottom portion of the container body, and
   hermetically closing the container body with the lid.

5. The moisture-proof container according to claim 3, wherein the inner case of the desiccant storage case has a plurality of second projections, which form the groove therebetween, at the outer circumferential wall of the inner case of the desiccant storage case.

6. The moisture-proof container according to claim 1, wherein the first projection is formed on an entire circumference of the inner circumferential wall of the container body,
   the outer circumferential wall of the inner case of the desiccant storage case has an outer diameter that matches an inner diameter of the container body, and
   a corner of the bottom portion of the inner case at which the groove is formed, is chamfered.

* * * * *